United States Patent
Hara

(10) Patent No.: US 7,142,704 B2
(45) Date of Patent: Nov. 28, 2006

(54) IMAGE DISPLAY SYSTEM

(75) Inventor: Shoji Hara, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 755 days.

(21) Appl. No.: 10/426,935

(22) Filed: May 1, 2003

(65) Prior Publication Data

US 2003/0227467 A1 Dec. 11, 2003

(30) Foreign Application Priority Data

May 1, 2002 (JP) ............... 2002-129819

(51) Int. Cl.
G06K 9/00 (2006.01)
H04N 5/253 (2006.01)
H04N 7/14 (2006.01)

(52) U.S. Cl. ............... 382/131; 382/166; 348/96

(58) Field of Classification Search ............... 382/128, 382/131, 132, 166, 264, 266; 348/364, 365, 348/96, 625, 672, 14.13, 14.07; 345/604, 345/690; 378/98.2, 98.12

See application file for complete search history.

(56) References Cited

U.S. PATENT DOCUMENTS

| | | | |
|---|---|---|---|
| 4,079,417 A * | 3/1978 | Scudder, III | 378/98.2 |
| 5,384,643 A * | 1/1995 | Inga et al. | 358/403 |
| 5,454,044 A | 9/1995 | Nakajima | |
| 5,456,255 A * | 10/1995 | Abe et al. | 600/443 |
| 5,461,682 A * | 10/1995 | Nomura | 382/232 |
| 5,608,813 A | 3/1997 | Nakajima | |
| 6,552,332 B1 * | 4/2003 | Kusaka et al. | 250/238 |

* cited by examiner

Primary Examiner—Sheela Chawan
(74) Attorney, Agent, or Firm—Sughrue Mion, PLLC

(57) ABSTRACT

A dynamic range compression processing and a plurality of other predetermined image processings are separately carried out on an original image data. A dynamic-range-compressed image is displayed on the basis of image data obtained by carrying out the dynamic range compression processing on the original image data and a plurality of otherwise-processed images are displayed on the basis of a plurality of pieces of image data obtained by carrying out the other predetermined image processings on the original image data. An otherwise-processed image is displayed on the basis of image data which is obtained by carrying out the other predetermined image processing on the same original image data as the original image data of the dynamic-range-compressed image which is displayed upon switching action by the operating means.

7 Claims, 8 Drawing Sheets

IMAGE DISPLAY SYSTEM

BACKGROUND OF THE INVENTION

1. Field of the Invention

This invention relates to an image display system, and more particularly to a system for displaying an image subjected to, for instance, dynamic range compression processing.

2. Description of the Related Art

There have been put into practice a CT (Computed Tomography) apparatus or an MRI (Magnetic Resonance Imaging) apparatus for showing in a slice a predetermined part of an object such as a human body. Generally a plurality of cross-sectional images of an object taken at different depths (in the direction perpendicular to the plane of the image) are obtained by the use of such an apparatus in order to know the three-dimensional conditions of the part.

The cross-sectional images are generally recorded as hard copies or displayed by, for instance, a CRT display after subjected to gradation processing so that they are adapted for reading.

In a medical image displayed by, for instance, a CRT, a plurality of areas of interest can be sometimes included. In such a case, the optimal processing condition generally differs by the area of interest. For example, in a chest CT image, the lung and the mediastinum are different in the optimal gradation processing condition. Conventionally, when an image includes a plurality of areas of interest, a plurality of images processed under different gradation processing conditions are displayed. For example, in the case of a chest CT image, an image gradation-processed under a processing condition suitable for reproducing an image adapted to reading the lung and an image gradation-processed under a processing condition suitable for reproducing an image adapted to reading the mediastinum are displayed side by side in one screen.

In the case where only one cross-section of the object part is displayed, displaying two images processed under different conditions in a screen gives rise to no problem in reading. However, in the case where a number of cross-sections of the object part are displayed in sequence, displaying two images processed under different conditions in a screen for each cross-section makes reading troublesome. That is, when reading the images, the reader must change the direction of his or her eyes from one image to the other on one screen each time the images of a different cross-section are displayed (generally requiring movement of his or her neck), which is very troublesome for the reader.

SUMMARY OF THE INVENTION

In view of the foregoing observations and description, the primary object of the present invention is to provide an image display system which makes it feasible to view a plurality of images processed under different conditions at a good workability.

In accordance with the present invention, there is provided an image display system comprising an image processing means which separately carries out a dynamic range compression processing and a plurality of other predetermined image processings on an original image data, an image display means which displays a dynamic-range-compressed image on the basis of image data obtained by carrying out the dynamic range compression processing on the original image data and a plurality of otherwise-processed images on the basis of a plurality of pieces of image data obtained by carrying out said other predetermined image processings on the original image data, an operating means for taking a switching action representing a demand for switching images displayed by the image display means, and a control means which causes the image display means to display an otherwise-processed image on the basis of image data which is obtained by carrying out said other predetermined image processing on the same original image data as the original image data of the dynamic-range-compressed image which is displayed by the image display means upon the switching action by the operating means.

The "dynamic range compression processing" is (1) a processing for compressing the overall dynamic range with the contrast in the signal range corresponding to a main object area of view or an area of interest held unchanged, or (2) a processing for compressing the overall dynamic range with the contrast of the structure of a main object area of view held unchanged. See, for instance, Japanese Unexamined Patent Publication No. 3(1991)-222577 and Japanese Patent Application No. 2002-117731. FIG. 8 is a view for briefly illustrating the dynamic range compression processing described above in (1). That is, in this processing, the image signal is transformed according to the characteristic curve a and the signal range corresponding to an area of non-interest (the area outside the area of interest) is reduced in contrast with the contrast in the signal range corresponding to the area of interest held unchanged, thereby compressing the overall dynamic range. FIGS. 9A and 9B are views for briefly illustrating the dynamic range compression processing described above in (2). That is, in this processing, the spatial frequency range corresponding to an area of non-interest (the area outside the area of interest) is reduced in contrast by transforming the signal values (which are originally as shown in FIG. 9A) as shown in FIG. 9B with the contrast in the spatial frequency range corresponding to the structure of the main object area held unchanged, thereby compressing the overall dynamic range.

Preferably, the original image data is image data representing a plurality of cross-sections of an object.

Preferably, the control means causes the image display means to display a plurality of dynamic-range-compressed images one by one and to display a plurality of said otherwise-processed images in place of the dynamic-range-compressed image upon the switching action by the operating means. In this case, preferably the control means is provided with a part designating means which designates a part of the dynamic-range-compressed image displayed by the display means upon the switching action by the operating means and causes the image display means to display otherwise-processed images which are processed under a condition suitable for reproducing an image of the part designated by the part designating means.

The control means may be arranged to cause the image display means to display a plurality of dynamic-range-compressed images one by one and to display a plurality of said otherwise-processed images together with the dynamic-range-compressed image upon the switching action by the operating means.

Further, the control means may be arranged to cause the image display means to display a plurality of dynamic-range-compressed images on one screen and the switching action is an action of selecting one of the dynamic-range-compressed images, the control means being further arranged to cause the image display means to display a plurality of otherwise-processed images on the basis of a plurality of pieces of image data which are obtained by carrying out said other predetermined image processings on the same original image data as the original image data of the selected dynamic-range-compressed image.

The dynamic-range-compressed image is sufficient to determine whether the image includes an abnormal shadow though it is less suitable for precise diagnosis for determining what is the abnormal shadow as compared with an image which has been processed under a condition set to be suitable for reading a particular part of the image.

For example, a dynamic-range-compressed CT image of a chest is an image close to, in the density and contrast, an image gradation-processed under a processing condition suitable for reproducing an image adapted to reading the mediastinum with the contrast of the lung held unchanged. Accordingly, whether the image includes an abnormal shadow can be determined on the basis of the dynamic-range-compressed image. However, since the relation between the signal value and the density of the image cannot be uniform in the dynamic-range-compressed image, an image gradation-processed under a processing condition suitable for reproducing an image adapted to reading the lung and an image gradation-processed under a processing condition suitable for reproducing an image adapted to reading the mediastinum are necessary for precise diagnosis.

The operator of the image display system of the present invention operates the operating means only when he or she finds an image including therein a suspected abnormal shadow to view an image processed under a processing condition suitable for precise diagnosis of the part of the suspected abnormal shadow.

With the image display system of the present invention, the reader need not change the direction of his or her eyes from one image to the other on one screen, reading of images can be simplified.

DESCRIPTION OF THE PREFERRED EMBODIMENTS

Figure 1:
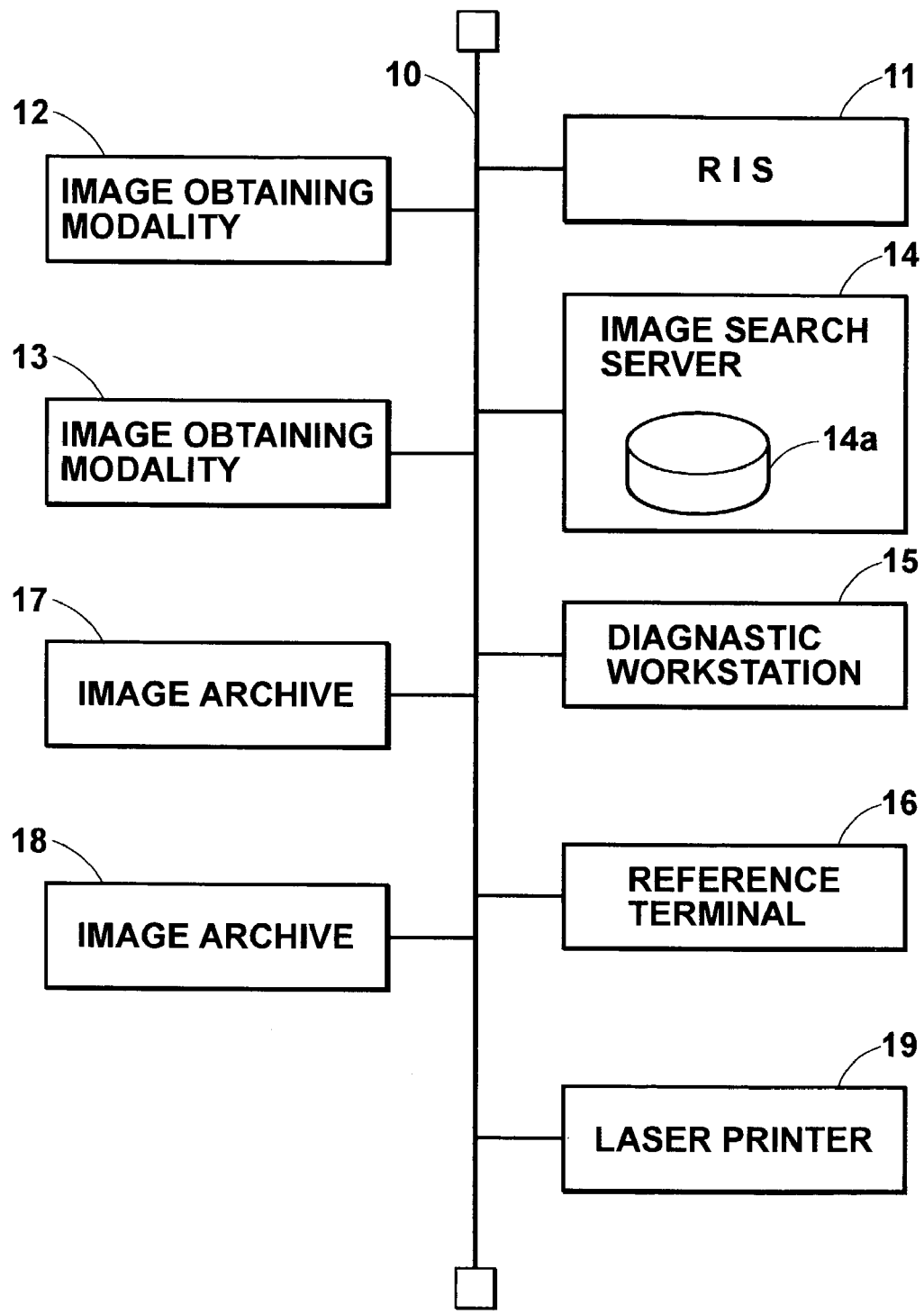
FIG. 1 is a block diagram showing in brief a medical network system provided with an image display system in accordance with a first embodiment of the present invention.

FIG. 1 is a block diagram showing a medical network system provided with an image display system in accordance with a first embodiment of the present invention. This system comprises a network 10 which may be a local area network (LAN) such as an Ethernet®, an FDDI or the like. The LAN may be connected to the internet or the like by way of a leased line or a public network such as an ISDN.

A radiology information system (RIS) 11, image obtaining modalities 12 and 13, an image search server 14, a diagnostic workstation (a terminal) 15, a reference terminal 16, image archives 17 and 18, and a laser printer 19 connected to the network 10.

The image obtaining modality 12 or 13 is a system for obtaining an image of an object as digital data such as CT, MRI, CR, RI or US. For example, the image obtaining modality 12 or 13 may obtain the digital data by digitizing an analog image signal obtained by taking an image of the object or by digitally reading an image recorded on a photographic film or the like.

The radiology information system (RIS) 11 is connected to terminals (not shown) in the department of radiology or other departments such as the department of surgery, the internal department or the like which make a request for taking a radiation image of the patient, and performs information transfer, information processing and/or the like in the department of radiology on the basis of information on the examination order (the order for examination to be carried out on the patient) transferred from the department which makes the request for taking a radiation image of the patient, information on image taking transferred from the image obtaining modality 12 or 13.

The image search server 14 comprises a computer system and constructs databases by storing image data obtained by the image obtaining modality 12 or 13 in the image archive 17 or 18 together with image searching information attached to each image (the name of the patient, the department which makes a request for taking the radiation image, the date of taking the image, and the like). In this manner, a number of pieces of image data are stored in the image archives 17 and 18.

The image search server 14 searches the databases for a desired image requested through the diagnostic workstation 15 or the reference terminal 16 and transfers the result of the search and image data obtained by the search to the diagnostic workstation 15 or the reference terminal 16.

The diagnostic workstation 15 is a terminal which is used by, for instance, a doctor in the department of radiology for making a diagnosis on the basis of a processed image after carrying out desired image-processing on the image data (for instance, by changing the parameter of the image processing).

The reference terminal 16 is a terminal solely for referring to image data and not provided with an image-processing function. The laser printer 19 outputs a visible image on the basis of processed image data. Outputting processed image data to the laser printer 19 is performed when the diagnostic workstation 15 issues an instruction to the image search server 14.

The image search server 14 constructs databases in a hard disc 14a and executes image search processing in the following manner. The image search server 14 is provided with an information obtaining means for obtaining image searching information attached to each image and a database constructing means, which execute respective processings according to a predetermined computer program.

That is, in this particular embodiment, the image search server 14 obtains information on the patient by receiving input of the examination order from the radiology information system (RIS) 11 thereby obtaining image searching information for the patient to be stored in the image archives 17 and 18, and stores the obtained information in the hard disc 14a, thereby constructing the databases.

When a request for searching an image is input from the diagnostic workstation 15 or the reference terminal 16, the image research server 14 searches the databases on the hard disc 14a for the requested image and outputs the result of search to the workstation 15 or the reference terminal 16.

When a request for obtaining an image is input from the diagnostic workstation 15 or the reference terminal 16 on the basis of the result of search, the image search server 14 takes out image data representing the requested image from the image archive 17 or 18 and outputs the image to the workstation 15 or the reference terminal 16.

Figure 2:
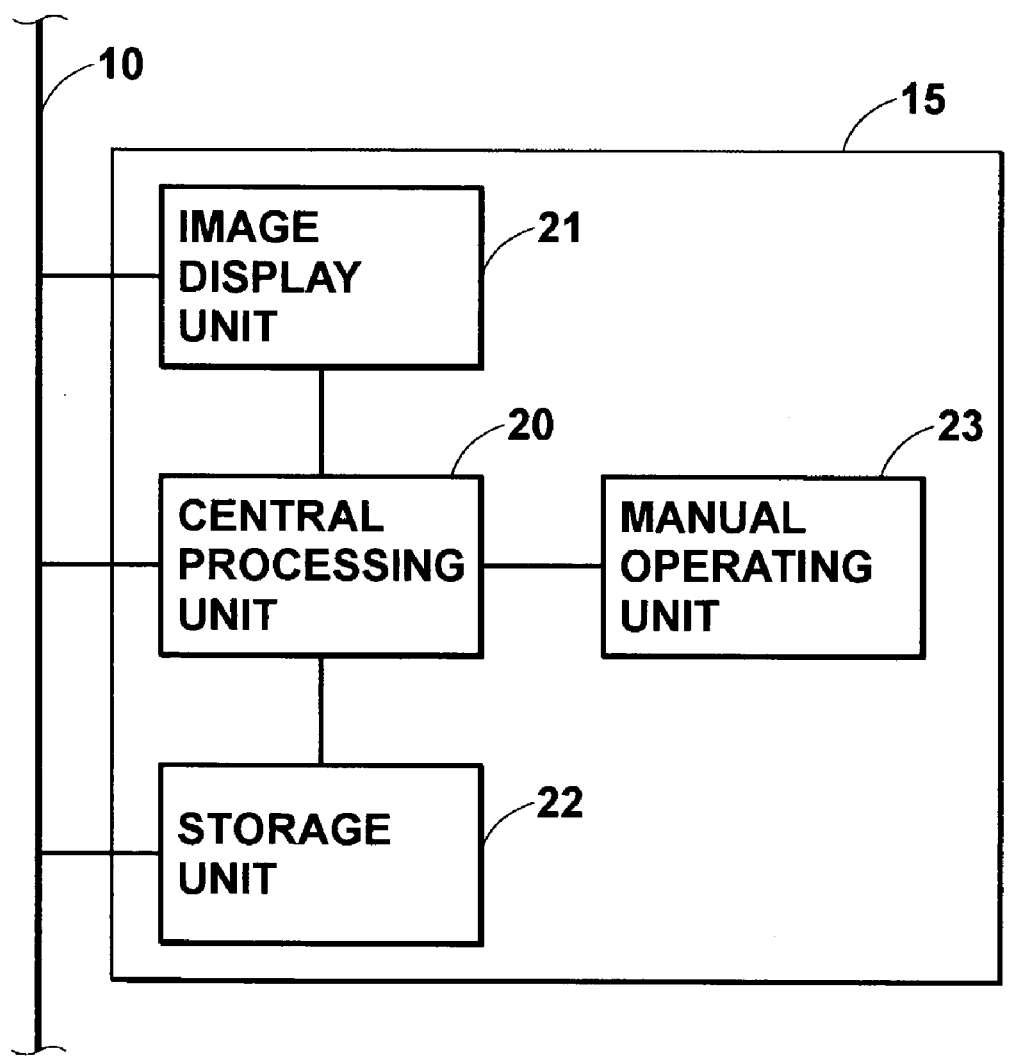
FIG. 2 is a block diagram showing in brief the image display system.

The diagnostic workstation 15 (the image display system of this embodiment) will be described in detail with reference to FIG. 2, hereinbelow. The diagnostic workstation 15 comprises a central processing unit 20 having therein an image processing system, an image display unit 21 which may comprise, for instance, a CRT connected to the central processing unit 20, a storage unit 22 which is connected to the central processing unit 20 to store result of temporary operation, and a manual operating unit 23 which may comprise, for instance, a keyboard and a mouse.

The central processing unit 20 causes the image display unit 21 to display an image on the basis of image data transferred from the image obtaining modality 12 or 13 or a medical image on the basis of image data read out from the image archive 17 or 18. The central processing unit 20 can display an image on the basis of the image data unchanged or on the basis of image data obtained by carrying out dynamic-range-compression processing and other predetermined processings on the image data. The kinds of the processings or the parameters to be used in the processings can be selected by the manual operating unit 23 on the basis of experience of the operator or the like so that an image suitable for diagnosis can be obtained. The doctor or the like operating the diagnostic workstation 15 diagnoses the patient on the basis of the image displayed.

Processing of a chest CT image by the central processing unit 20 which also functions as the control means will be described, hereinbelow. When an original image data representing a plurality of CT images of cross-sections taken at a plurality of points spaced from each other in the direction of the axis of the body is input, the central processing unit 20 carries out a dynamic-range-compression processing, a gradation processing under a processing condition suitable for reproducing an image adapted to reading the lung and a gradation processing under a processing condition suitable for reproducing an image adapted to reading the mediastinum on the original image data representing the cross-sectional image at each point and causes the storage unit 22 to temporarily store the three pieces of image data processed in three-ways.

Figure 3:
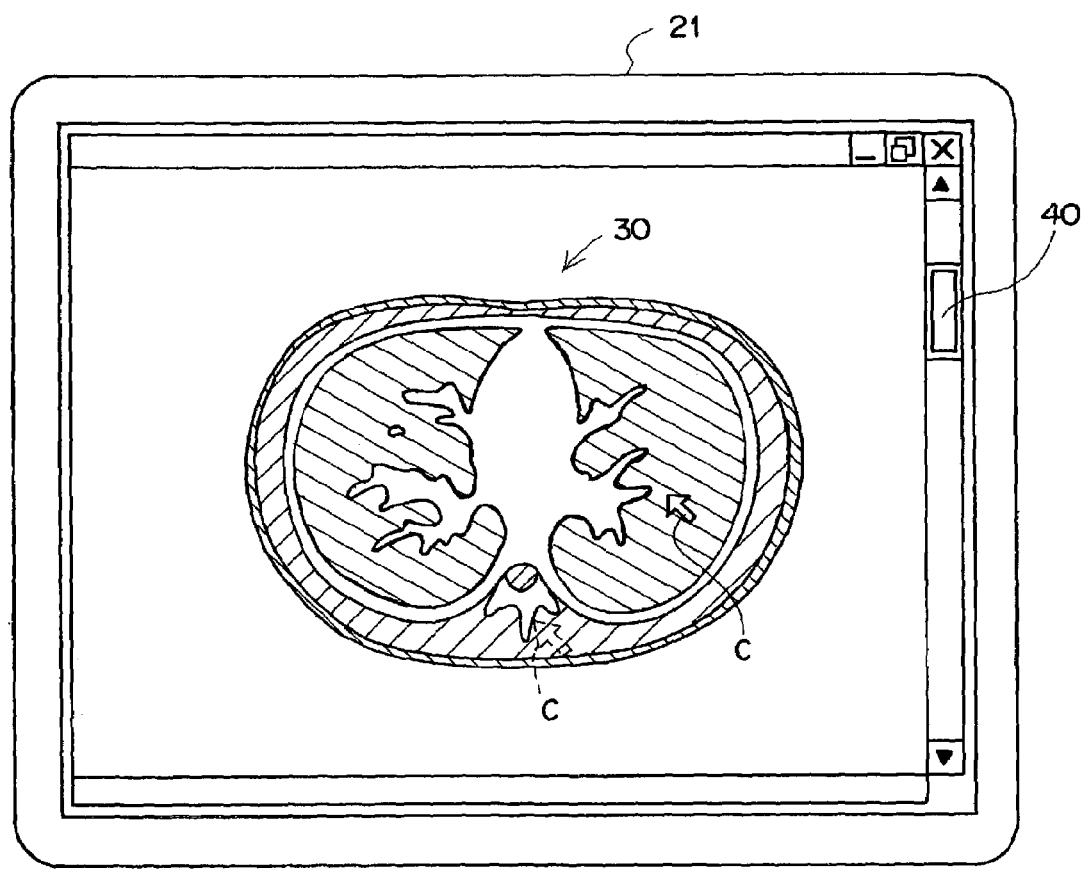
FIG. 3 is a view showing an image displayed by the display means of the image display system shown in FIG. 2.

Then the central processing unit 20 causes the image display unit 21 to display the dynamic-range compressed image 30, for instance, as shown in FIG. 3. A dynamic-range compressed image 30 of a cross-section in a first slice position (e.g., an uppermost slice position) is first displayed and as a scroll bar 40 on the screen is moved downward by the mouse or the like of the manual operating unit 23, dynamic-range compressed images 30 of cross-sections in second, third, fourth . . . slice positions are displayed in sequence.

In the dynamic-range compressed image 30 thus displayed, both the lung (the part where a cursor C is shown by the solid line in FIG. 3) and the mediastinum (the part where a cursor C is shown by the broken line in FIG. 3) are reproduced to such an extent that whether there is an abnormal shadow therein can be seen. That is, the operator views the dynamic-range compressed images 30 in sequence and when the operator sees an abnormal shadow in a dynamic-range compressed image 30, he or she stops moving the scroll bar 40 and moves the cursor C in the vicinity of the suspected abnormal shadow. Thereafter, the operator takes a predetermined switching action, for instance, double-clicking the mouse or pushing a particular key of the keyboard.

When a switching action is taken, a gradation-processed image is displayed on the basis of image data which is obtained by carrying out gradation processing on the same original image data as the original image data of the dynamic-range-compressed image which is displayed by the image display unit 21 upon the operator taking the switching action (that is, on the basis of image data which is obtained by carrying out gradation processing on the original image data which is taken in the same slice position as the original image data of the dynamic-range-compressed image which is displayed by the image display unit 21 upon the operator taking the switching action). One of an image gradation-processed under a processing condition suitable for reproducing an image adapted to reading the lung and an image gradation-processed under a processing condition suitable for reproducing an image adapted to reading the mediastinum is selected according to the position of the cursor C in the following manner.

Figure 4:
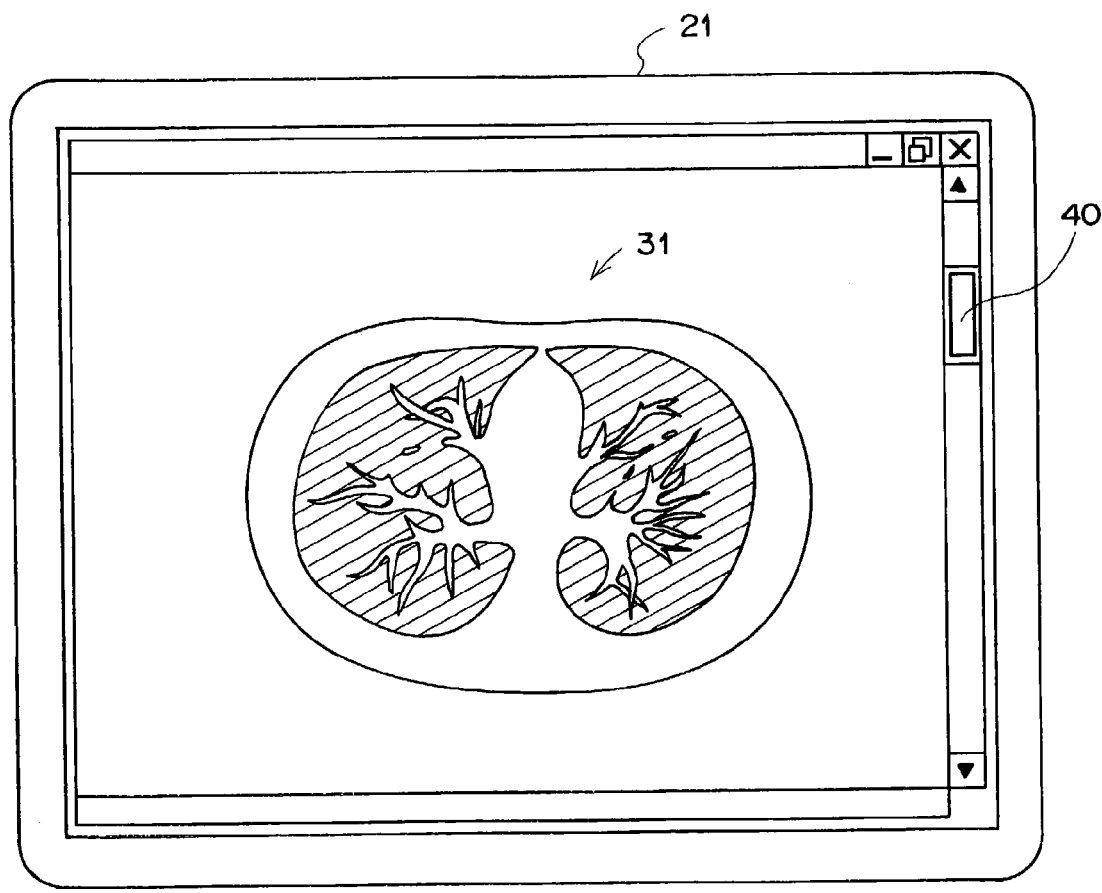
FIG. 4 is a view showing another image displayed by the display means of the image display system shown in FIG. 2.
Figure 5:
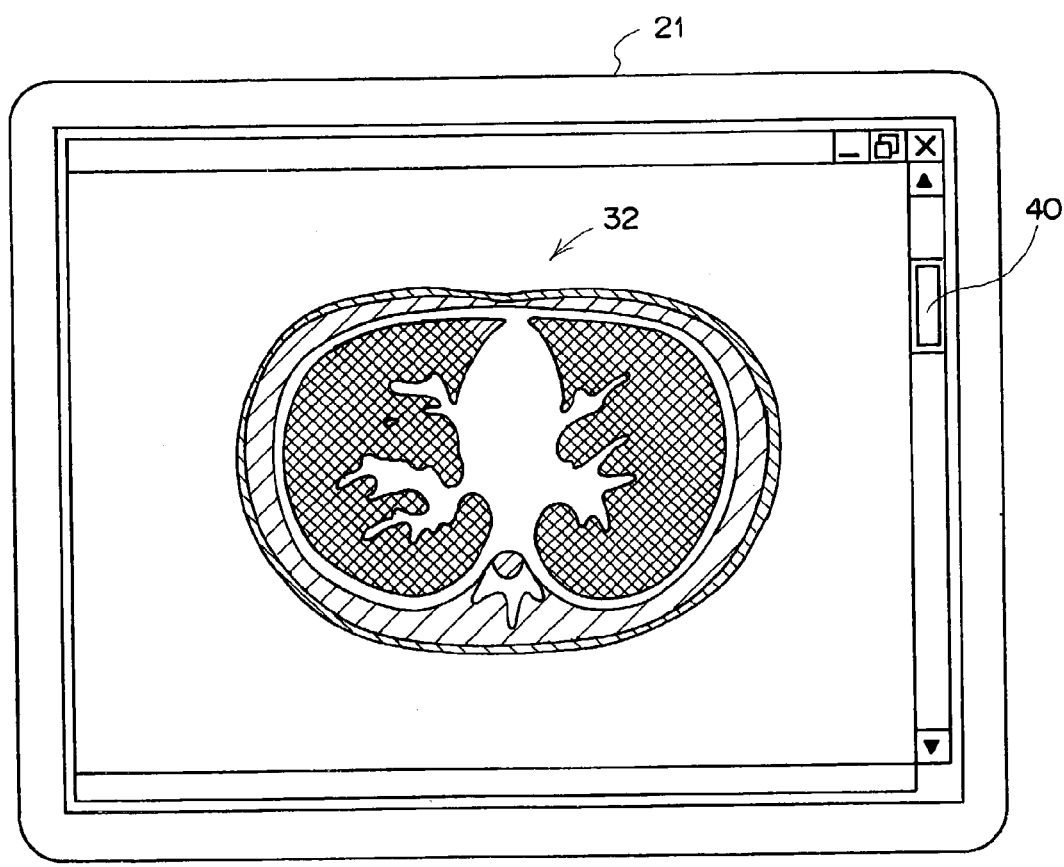
FIG. 5 is a view showing still another image displayed by the display means of the image display system shown in FIG. 2.

That is, when the cursor C is on the image of the lung as shown by the solid line in FIG. 3, an image 31 gradation-processed under a processing condition suitable for reproducing an image adapted to reading the lung is displayed as shown in FIG. 4. Whereas, when the cursor C is on the image of the mediastinum as shown by the broken line in FIG. 3, an image 32 gradation-processed under a processing condition suitable for reproducing an image adapted to reading the mediastinum is displayed as shown in FIG. 5. Whether the cursor C is on the image of the lung or on the image of the mediastinum is preferably judged on background while the dynamic-range-compressed images 30 are displayed.

As can be understood from the description above, in this embodiment, by simply changing the position of the cursor C, an image 31 gradation-processed under a processing condition suitable for reproducing an image adapted to reading the lung or an image 32 gradation-processed under a processing condition suitable for reproducing an image adapted to reading the mediastinum can be selectively displayed. This arrangement is advantageous over the arrangement where the switching action requires operation of button or the keyboard in that the eyes need not be removed from the screen of the image display unit 21 and reading of the shadow can be more efficiently effected.

Further, since whether an abnormal shadow exists can be judged by viewing a single image (a dynamic-range-compressed image 30), reading of the shadow is facilitated as compared with when whether an abnormal shadow exists is judged by viewing images while moving the eyes from a view to the other view (e.g., gradation-processed images 31 and 32).

Figure 6:
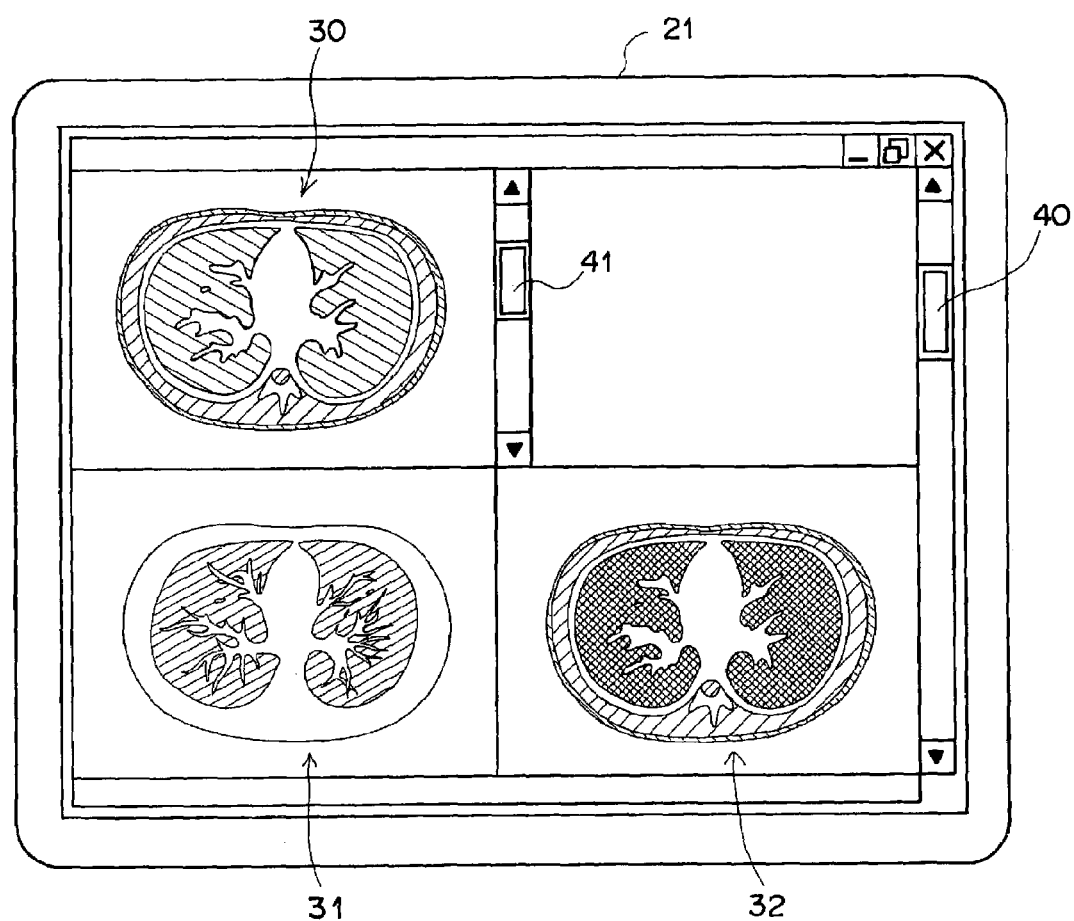
FIG. 6 is a view showing an image displayed by the display means of an image display system in accordance with a second embodiment of the present invention.

An image display system in accordance with a second embodiment of the present invention will be described, hereinbelow, with reference FIG. 6. In FIG. 6, the elements analogous to those shown in FIGS. 3 to 5 are given the same reference numerals and will not be described here unless necessary.

The image display system of this embodiment differs from that of the first embodiment in that the central processing unit 20 causes the image display unit to display the gradation-processed images 31 and 32 in a different way. That is, in this embodiment, a dynamic-range compressed image 30 of a cross-section in a first slice position (e.g., an uppermost slice position) is first displayed at one of the frames of the screen as shown in FIG. 6 and as a scroll bar 41 on the frame is moved downward by the mouse or the like of the manual operating unit 23, dynamic-range compressed images 30 of cross-sections in second, third, fourth . . . slice positions are displayed at the frame in sequence.

In this embodiment, stopping the scroll bar 41 is considered to be a switching action. That is, when the operator finds an abnormal shadow and stops the scroll bar 41, gradation-processed images 31 and 32 are displayed at second and third frames on the basis of a pair of pieces of image data which are obtained by carrying out gradation processing on the same original image data as the original image data of the dynamic-range-compressed image which is displayed by the image display unit 21 (that is, on the basis of pieces of image data which are obtained by carrying out gradation processing on the original image data which is taken in the same slice position as the original image data of the dynamic-range-compressed image which is displayed by the image display unit 21 upon the operator stops the scroll bar 41). The gradation-processed images 31 and 32 are an image gradation-processed under a processing condition suitable for reproducing an image adapted to reading the lung and an image gradation-processed under a processing condition suitable for reproducing an image adapted to reading the mediastinum as in the first embodiment.

Also in this embodiment, since whether an abnormal shadow exists can be judged by viewing a single image (a dynamic-range-compressed image 30), reading of the shadow is facilitated as compared with when whether an abnormal shadow exists is judged by viewing images while moving the eyes from a view to the other view (e.g., gradation-processed images 31 and 32).

When the dynamic-range compressed image 30 of the cross-section in the first slice position is displayed, the gradation-processed images 31 and 32 for the cross-section may be or need not be displayed.

Figure 7:
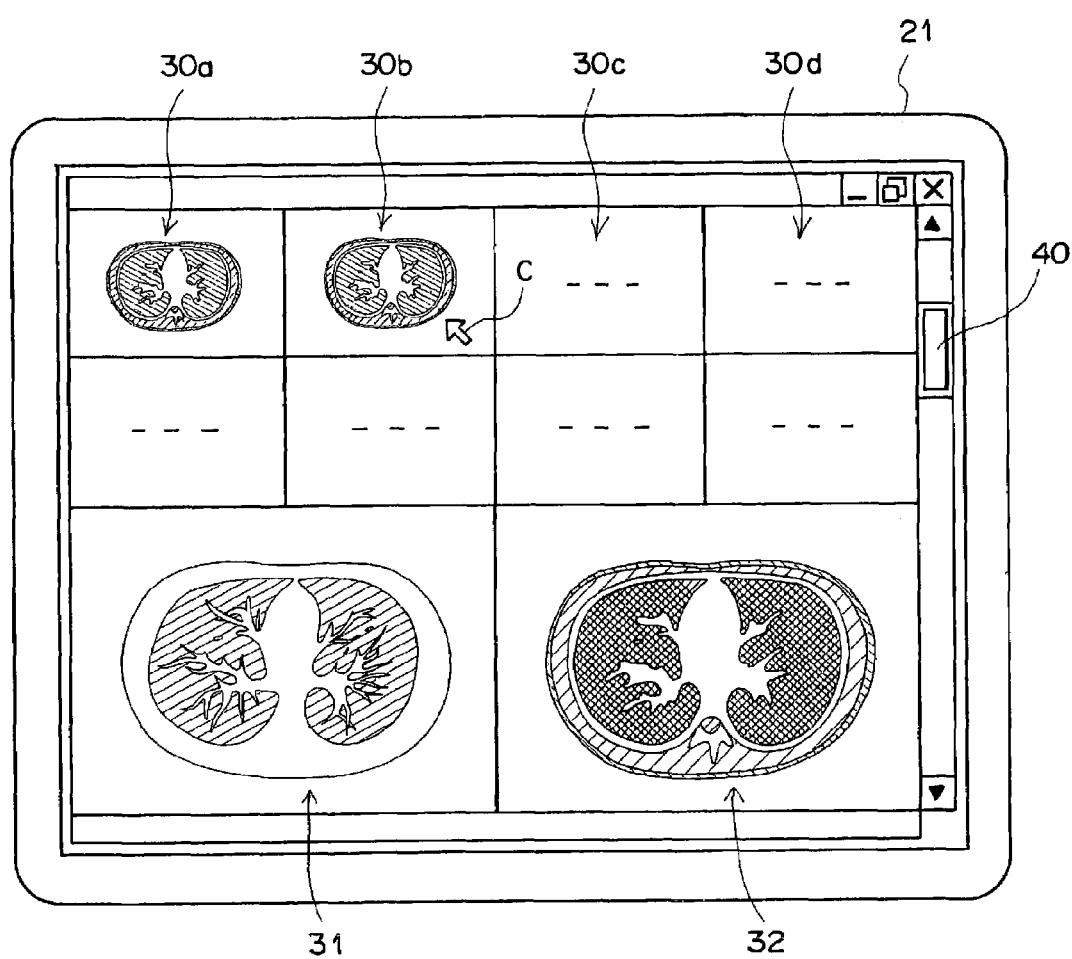
FIG. 7 is a view showing an image displayed by the display means of an image display system in accordance with a third embodiment of the present invention.
Figure 8:
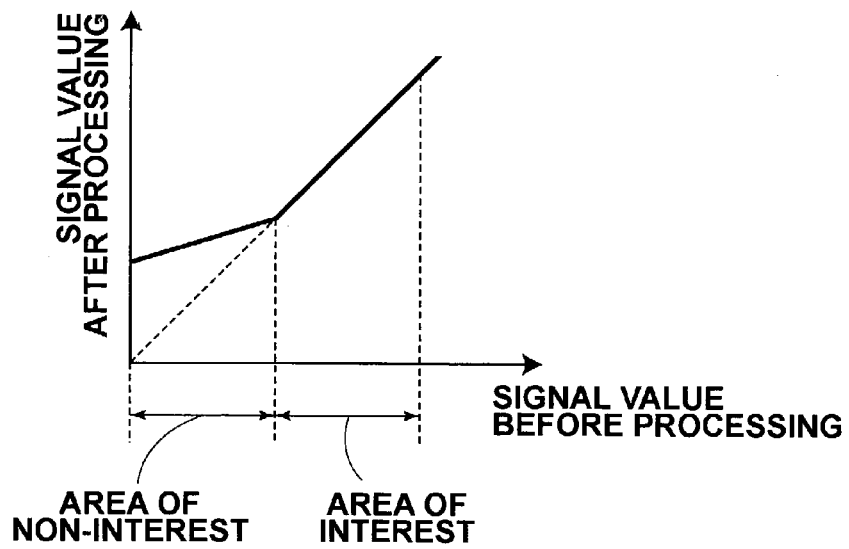
FIG. 8 is a view for illustrating an example of the dynamic-range-compression processing.
Figure 9A:
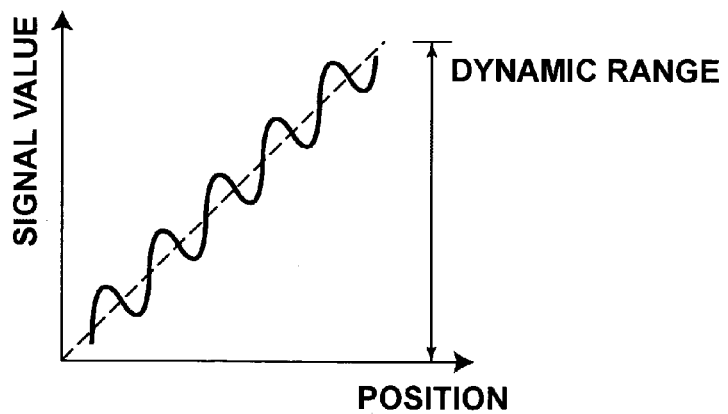
FIGS. 9A and 9B are views for illustrating another example of the dynamic-range-compression processing.
Figure 9B:
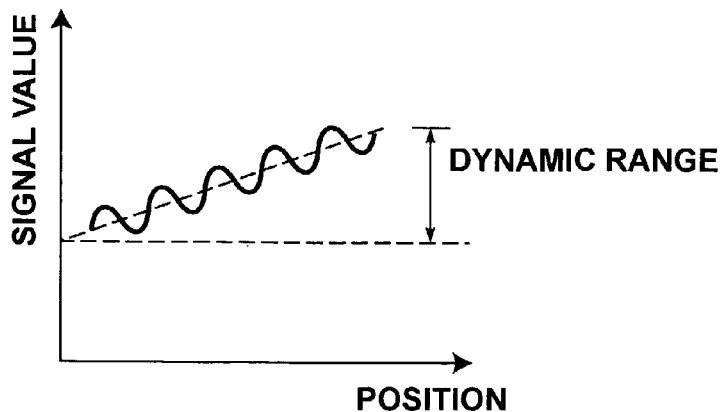

An image display system in accordance with a third embodiment of the present invention will be described, hereinbelow, with reference FIG. 7. In FIG. 7, the elements analogous to those shown in FIGS. 3 to 5 are given the same reference numerals and will not be described here unless necessary. The image display system of this embodiment differs from that of the first embodiment in that the central processing unit 20 causes the image display unit to display the gradation-processed images 31 and 32 in a different way. That is, in this embodiment, dynamic-range compressed images 30a, 30b, 30c . . . of cross-sections in first, second, third . . . slice positions are displayed in a screen in a tile view as shown in FIG. 7.

When the operator takes a predetermined switching action, for instance, double-clicking the mouse or pushing a particular key of the keyboard, after moving the cursor C to one of the dynamic-range compressed images 30a, 30b, 30c . . . of cross-sections in first, second, third . . . slice positions, gradation-processed images 31 and 32 are displayed below the dynamic-range compressed images 30a, 30b, 30c . . . on the basis of a pair of pieces of image data which are obtained by carrying out gradation processing on the same original image data as the original image data of the selected dynamic-range-compressed image (that is, on the basis of pieces of image data which are obtained by carrying out gradation processing on the original image data which is taken in the same slice position as the original image data of the selected dynamic-range-compressed).

The gradation-processed images 31 and 32 are an image gradation-processed under a processing condition suitable for reproducing an image adapted to reading the lung and an image gradation-processed under a processing condition suitable for reproducing an image adapted to reading the mediastinum as in the first embodiment.

Also in this embodiment, since whether an abnormal shadow exists can be judged by viewing the dynamic-range compressed images 30a, 30b, 30c . . . , reading of the shadow is facilitated as compared with when whether an abnormal shadow exists is judged by viewing images while moving the eyes from a view to the other view (e.g., gradation-processed images 31 and 32).

Before one of the dynamic-range compressed images 30a, 30b, 30c . . . is selected, the gradation-processed images 31 and 32 for the cross-section in the first slice position may be displayed or no gradation-processed image may be displayed.

What is claimed is:

1. An image display system comprising:
   an image processing means which separately carries out a dynamic range compression processing and a plurality of other predetermined image processings on an original image data;
   an image display means which displays a dynamic-range-compressed image on the basis of image data obtained by carrying out the dynamic range compression processing on the original image data and a plurality of otherwise-processed images on the basis of a plurality of pieces of image data obtained by carrying out said other predetermined image processings on the original image data;
   an operating means for taking a switching action representing a demand for switching images displayed by the image display means; and
   a control means which causes the image display means to display an otherwise-processed image on the basis of image data which is obtained by carrying out said other predetermined image processing on the same original image data as the original image data of the dynamic-range-compressed image which is displayed by the image display means upon the switching action by the operating means, wherein the control means causes the image display means to display a plurality of dynamic-range-compressed images on one screen and the switching action is an action of selecting one of the dynamic-range-compressed images, the control means being further arranged to cause the image display means to display a plurality of otherwise-processed images on the basis of a plurality of pieces of image data which are obtained by carrying out said other predetermined image processings on the same original image data as the original image data of the selected dynamic-range-compressed image.

2. An image display system as defined in claim 1 in which the original image data is image data representing a plurality of cross-sections of an object.

3. An image display system as defined in claim 2 in which the control means causes the image display means to display a plurality of dynamic-range-compressed images one by one and to display a plurality of said otherwise-processed images in place of the dynamic-range-compressed image upon the switching action by the operating means.

4. An image display system as defined in claim 2 in which the control means causes the image display means to display a plurality of dynamic-range-compressed images one by one and to display a plurality of said otherwise-processed images together with the dynamic-range-compressed image upon the switching action by the operating means.

5. An image display system as defined in claim 2 in which the control means causes the image display means to display a plurality of dynamic-range-compressed images on one screen and the switching action is an action of selecting one of the dynamic-range-compressed images, the control means being further arranged to cause the image display means to display a plurality of otherwise-processed images on the basis of a plurality of pieces of image data which are obtained by carrying out said other predetermined image processings on the same original image data as the original image data of the selected dynamic-range-compressed image.

6. An image display system as defined in claim 1 in which the control means causes the image display means to display a plurality of dynamic-range-compressed images one by one and to display a plurality of said otherwise-processed images in place of the dynamic-range-compressed image upon the switching action by the operating means.

7. An image display system as defined in claim 1 in which the control means causes the image display means to display a plurality of dynamic-range-compressed images one by one and to display a plurality of said otherwise-processed images together with the dynamic-range-compressed image upon the switching action by the operating means.

* * * * *